United States Patent [19]
Walters et al.

[11] Patent Number: 5,861,175
[45] Date of Patent: Jan. 19, 1999

[54] USE OF FLUOROCARBONS FOR DIAGNOSIS AND TREATMENT OF ARTICULAR DISORDERS

[75] Inventors: Mark A. Walters, San Diego; Ronald M. Hopkins, Escondido; David H. Klein, Carlsbad, all of Calif.

[73] Assignee: Alliance Pharmaceutical Corp., San Diego, Calif.

[21] Appl. No.: 616,260

[22] Filed: Mar. 15, 1996

[51] Int. Cl.$^6$ ............................. A61K 9/10; A61K 31/755
[52] U.S. Cl. ........................ 424/486; 424/423; 424/426; 424/501; 514/829
[58] Field of Search ...................... 424/424, 501, 424/422, 423, 426, 486; 514/825, 937–38, 944

[56] References Cited

U.S. PATENT DOCUMENTS

| | | |
|---|---|---|
| 3,697,653 | 10/1972 | Ongley . |
| 4,828,828 | 5/1989 | Trager et al. . |
| 4,865,836 | 9/1989 | Long, Jr. . |
| 4,927,623 | 5/1990 | Long, Jr. . |
| 4,951,673 | 8/1990 | Long . |
| 4,987,154 | 1/1991 | Long, Jr. . |
| 4,993,415 | 2/1991 | Long ........................................ 128/653 |
| 5,143,724 | 9/1992 | Leshchiner et al. . |
| 5,149,319 | 9/1992 | Unger ...................................... 424/450 |
| 5,173,298 | 12/1992 | Meadows ................................ 424/423 |
| 5,470,885 | 11/1995 | Fuhrman et al. . |
| 5,496,535 | 3/1996 | Kirkland . |

FOREIGN PATENT DOCUMENTS

| | | |
|---|---|---|
| 0307863 | 3/1989 | European Pat. Off. . |
| 9508985 | 4/1995 | WIPO . |

OTHER PUBLICATIONS

Tang–Liu, et al. "Lenticular Uptake and Distribution of Xenobiotics and Amino Acids" J. of Ocular Pharmacology 8(3):267–277 (1992).

Hughes, et al. "Effect of Acylation on the Ocular Disposition of Acyclovir II: Corneal Permeability and Anti–HSV 1 Activity of 2'–Esters in Rabbit Epithelial Keratitis" J. of Ocular Pharmacology 9(4): 299–309 (1993).

Hageluken, et al. "Lipophilic β–Adrenoceptor Antagonists and Local Anesthetics Are Effective Direct Activators of G–Proteins" Biochemical Pharmacology 47(10): 1789–1795 (1994).

Moriguchi, et al. "Simple Method of Calculating Octanol/Water Partition Coefficient"Chem. Pharm. Bull. 40(1): 127–130 (1992).

Yokogawa, et al. "Relationships inthe Structure–Tissue Distribution of Basic Drugs in the Rabbit" Pharmaceutical Res. 7(7): 691–696 (1990).

*Primary Examiner*—Edward J. Webman
*Attorney, Agent, or Firm*—Knobbe, Martens, Olson & Bear, LLP

[57] ABSTRACT

Methods for the diagnosis and treatment of articular disorders comprising the use of fluorocarbons are disclosed. The methods provide for the introduction of a fluorocarbon into an articular region to replace or augment natural synovial fluid. The introduced fluorocarbons, which may be in various forms including liquids, gels or emulsions, provide articular lubrication and cushioning which is effective for the treatment of disorders such as osteoarthritis and rheumatoid arthritis. Additionally, the methods of the present invention may be used to provide high resolution articular images, reduce articular inflammation and introduce bioactive agents to the articular region.

48 Claims, No Drawings

USE OF FLUOROCARBONS FOR DIAGNOSIS AND TREATMENT OF ARTICULAR DISORDERS

FIELD OF THE INVENTION

The present invention relates to therapeutic and diagnostic methods for the management of orthopedic disorders. More particularly, the present invention relates to the administration of fluorocarbons for the treatment or diagnosis of various articular disorders.

BACKGROUND OF THE INVENTION

One of the most significant events in the evolution of animal physiology was the internalization of the skeletal framework. In a broad sense, it allowed for substantial increases in size while retaining the mobility necessary to exploit new environments. Moreover, in higher organisms the skeletal system carries out several important functions. Fundamentally, it provides mechanical support for the tissues of the body and assists in the maintaining the body's natural mineral balance. It also exhibits a protective nature, reducing the potential for harm to delicate internal organs. Perhaps most importantly, the skeletal system is a dynamic structure incorporating numerous joints and providing a framework on which muscles can act to allow motion. Responsive to neural signals, this coordinated interaction is the basis for all voluntary movement.

The adult human skeleton is made up of 206 individual bones. The sites where the bones come together are commonly called joints (arthroses) or points of articulation. In normal operation, joints efficiently function to provide smooth, painless, stable, force transmission between one bone and the next with little effort. For the average adult individual, the joints cycle more than one million times a year, typically without injury or mishap. The hip, knee and ankle joints transmit forces of three times body weight with the simplest of activities such as walking, and over seven times the body weight when undergoing motion related to climbing stairs. Because much of the force transmitted across a joint is due to agonistic muscle contraction, the force per unit area carried by all extremity joints is similar.

Based on the nature of their connective tissue, joints are generally classified as belonging to one of two principal groups. In the first group, connective tissues remain solid (synarthroses). These solid joints are further classified as being fibrous joints or cartilaginous joints based on the most prevalent type of connective tissue. Fibrous joints tend to be articulations in which the surfaces of the bones are fastened together by intervening fibrous tissue. Such joints, including those between cranial bones, tend to allow little appreciable motion. Cartilaginous joints include synchondroses (primary cartilaginous joints) and symphyses (secondary cartilaginous joints) each of which may allow limited movement. The former are essentially growth mechanisms and are found where two separate but adjacent regions of ossification occur within a continuous mass of hyaline cartilage. In most cases, the cartilage is converted ultimately to bone and the synchondrosis is replaced by complete bony union, i.e. a synostosis. Symphyses, including the intervertebral discs, consist of two well-defined, hyaline cartilage-covered bones bonded by a strong, solid connective tissue such as fibrocartilage.

The second major group of joints, the predominant form of joint in the human body, are termed diarthroses or synovial joints. Synovial joints, which allow for a wide range of motion, incorporate a fluid filled cavity (the articular cavity) having a membrane known as the synovium. The synovium (or synovial membrane), richly supplied by both blood vessels and lymphatics, terminates at the margin of articular cartilage and is supported by the fibrous tissue defining the cavity or capsule. Only a few cell layers thick under normal circumstances, the synovium helps regulate the amount of liquid in a joint by secreting and absorbing synovial fluid. The synovial fluid plays an important role in lubricating and separating the bone and cartilaginous surfaces comprising the joint. More specifically, the bone surfaces are typically covered by articular cartilage, a specialized form of hyaline cartilage, which has a very low coefficient of friction. Sliding contact is facilitated by the presence of the synovial fluid, which, among other functions, provides for lubrication and maintenance of the living cells in the cartilage. Where the congruity between the bones is low there may also be an articular disc or meniscus of fibrocartilage. The purpose of this fibrocartilage is uncertain although it has been suggested that it plays a part in shock absorption, improvement of fit between surfaces and spreading of weight over a larger area. In any case, the synovial joints allow an impressive array of movements while successfully supporting immense loads.

The presence of healthy cartilaginous tissue is critical for the effective operation of synovial joints. Bathed by synovial fluid, cartilage provides a smooth, relatively malleable surface allowing for almost frictionless movement. Histologically, articular cartilage is avascular and lacking in nerve structures. It contains a relatively small number of cells (chondrocytes) in a stiff, gel-like extracellular matrix that is permeated by a network of collagen fibers. Synthesis, and to some extent degradation, of the cartilage matrix is undertaken by the chondrocytes. The unusual mechanical characteristics of cartilage are a result of the unique architectural combination as well as chemical interactions between the components. Mechanically, articular cartilage can be considered to be a fluid-filled, permeable, porous solid. It is efficient at resisting the large compressive forces generated by weight transmission during movement and its elasticity dissipates the effect of concussion. During normal joint operation, the cartilage is subjected to both mechanical distortion of the matrix and, as a result of movement of interstitial fluid in and out of the tissue, changes in volume. The movement of synovial fluid, both within the cartilage and in the articular cavity, is extremely important to proper joint function.

Synovial fluid is a dialysate of blood plasma into which hyaluronate, a glycosaminoglycan of high molecular weight is secreted by the synovial membrane. The high levels of hyaluronate dissolved in the synovial fluid tend to make it fairly viscous under normal physiological conditions. In humans, the volume of synovial fluid found in the joints is typically on the order of a few tenths of a milliliter to several milliliters which is deposited on, and permeates, the cartilage and other surfaces within the articular cavity. Besides providing the articular cartilage its smooth texture and appearance, synovial fluid is found in the bursa (small synovium lined cavities associated with ligaments) where it provides lubrication for the tendon sheaths. Collectively, the bursa and articular cavity are known as synovial cavities. The dispersion of the fluid on the critical parts of the joint plays a decisive role in transmuting the dry resistant surfaces into effective load bearing structures exhibiting very low friction. For instance, it has been reported that the friction between articular cartilage surfaces is one third that of ice on ice. Yet, the efficiency of the lubrication depends, at least in part, on the quality and smoothness of the cartilage. In joints exhibiting damaged or degenerate cartilage, surface irregularities impair the lubricating properties of the synovial fluid and increase the rate of wear. Accordingly, while the initial disruption of the cartilage may occur for any one of a number of reasons, destruction of the joint is often due to a reduction in lubrication efficiency and repetitive insult to the tissue.

Several mechanisms have been proposed to explain the degree of lubrication and/or cushioning provided by the synovial fluid. For example, fluid film lubrication, involving a relatively thick layer of liquid interposed between the surfaces, is generally accepted to play a role in joint function. Different forms of fluid film lubrication that act in synovial lubrication, depending on the loading of the joint, include hydrostatic, hydrodynamic, squeeze-film and elastohydrodynamic. It has also been proposed that, under certain conditions, boundary layer lubrication may occur. In this case, it is believed that a layer of water and glycoproteins adheres to each surface thus reducing the amount of direct contact. Moreover, solvent cohesion during boundary layer lubrication allows the synovial fluid to function as an adhesive, thereby promoting joint stability. Solvent cohesion is apparently the result of hydrogen bonding where the bonds have a relatively high tensile strength but little or no resistance to shear. Such a system enables opposing surfaces to slide freely across each other but limits their distraction.

Although normally functioning joints provide pain free, efficient movement, this is not generally the case when the joint has been damaged. Deterioration of joint function may lead to chronic pain, lack of mobility and, in extreme cases, total disability or even death. Unfortunately a multitude of diseases can affect the joints. Some may occur due to infection while others are the result of autoimmune disorders. In yet other cases, the joints may be functionally impaired or damaged by congenital disorders, age, trauma or repetitive mechanical stress over an extended period of time. Irrespective of the etiology, progressive and irreversible physiological degeneration often results. Quite often the synovial fluid in the joint (or joints) is lost or reduced in volume, thereby exacerbating the problem. Typically, degenerated cartilage is shed into the bursa or articular cavity where it is engulfed by the synovium. This leads to chronic reactive hyperemia in the synovial membrane with corresponding fibrosis and loss of elasticity in the subsynovial tissue. Gradually adhesions obliterate the synovial space and reduce or eliminate the synovial fluid. The loss of structural integrity leads to swelling, inflammation, and a reduction of joint mobility, a condition commonly known as rheumatism or arthritis.

In the past, rheumatism was the generic name for pain and stiffness associated with joints, muscles and related structures. Arthritis is more properly used where degeneration results in the inflammation of joints or connective tissue. However, the term is still often used generically to describe cases where inflammation does not occur. It is estimated that up to 33% of all adults are currently affected, at least temporarily, by some form of articular disorder. Of the more than 100 different types of articular disorder commonly termed "arthritis", the most common are osteoarthritis, rheumatoid arthritis, gout, pseudogout and ankylosing spondylitis. These five conditions account for more than half of all types of joint disease diagnosed today. Other less common, though still serious, types of arthritis include juvenile arthritis, lupus, scleroderma, chondromalacia patellae, and infectious arthritis. Still other types of articular disorders involve inflammation or irritation of the structures supporting the joint, such as muscles, tendons and ligaments. These condition include bursitis, tendinitis, fibrositis and polymyositis.

By far, the most prevalent articular disorders are rheumatoid arthritis and osteoarthritis which is also known as degenerative joint disease. Rheumatoid arthritis, thought to be an autoimmune disorder, is the result of an inflammation of the synovial membrane. Peak onset of the disorder occurs in the 30s and 40s and afflicts women three times more often than men. In extreme cases, chronic inflammation erodes and distorts the joint surfaces and connective tissue resulting in severe articular deformity and constant pain. Moreover, rheumatoid arthritis often leads to osteoarthritis, further compounding the destruction of the joint. The most common articular disorder, osteoarthritis is characterized by degenerative changes in the surface of the articular cartilage. Alterations in the physicochemical structure of the cartilage make it less resistant to compressive and tensile forces. Finally complete erosion occurs, leaving the subchondral bone exposed and susceptible to wear. Joints of the knees and hands are most often affected, followed by the spine, hips, ankles and shoulder. In both rheumatoid arthritis and osteoarthritis, degeneration of the weight bearing joints such as the hips and knees can be especially debilitating and often requires surgery to relieve pain and increase mobility.

No means currently exist for halting or reversing the degenerative changes brought about by these disorders. At the same time, approximately 37 million Americans seek symptomatic relief in the form of prescription drugs. In such cases nonsteroidal, anti-inflammatory drugs (NSAIDS) are most often prescribed. While these compounds often alleviate the arthritic symptoms, they are not without side effects such as nausea and gastrointestinal ulceration. Another class of commonly prescribed compounds are corticosteroid such as triamcinolone, prednisolone and hydrocortisone. Yet, the long term use of such measures increases the chance of undesirable side effects and is often contraindicated. In addition to difficulties in determining effective dosages, a number of adverse reactions have been reported during intra-articular steroid treatment. As a result, the use of corticosteroid treatments in the management of articular disorders is currently being reassessed.

Formulations of hyaluronic acid, including gels and slurries as described in U.S. Pat. No. 5,143,724, have also been proposed for use in the treatment of arthritis. However, the use of such treatments has been limited as hyaluronic acid is reported to lubricate only the soft tissues of the joint which are not subject to heavy loading. Further, as with more conventional treatments, adverse side effects have been observed following the intra-articular administration of the formulation. Significantly, patients with clinical histories of local adverse reactions to the hyaluronic acid treatment are reportedly susceptible to severe permanent joint damage. Accordingly, widespread use of the disclosed formulations has yet to be achieved.

In addition to the intra-articular injection of natural polymers such as hyaluronan, the administration of synthetic polymers has also been used for the management of articular disorders. For example, U.S. Pat. No. 4,828,828 discloses methods of treating degenerative joint disease through the intra-articular injection of meth(acrylamide) (co)-polymers in the form if a gel. However, acrylamide monomers are known to be potent neurotoxins making such gels undesirable for long term therapeutic administration. Questions involving breakdown products and bioincorporation of the constituent material complicate necessary regulatory approval. Similarly, U.S. Pat. No. 3,697,653 describes a method of treating osteoarthritic joints with polysiloxanes. While the disclosed materials possess some of the desired qualities for the proposed use, the presence of free silicone and silicone derivatives have recently been associated with immune disorders and connective tissue disease. In particular, silicone breast implants incorporating polysiloxanes have been implicated in the etiology of autoimmune disorders, immune suppression, connective tissue disease and, perhaps most importantly, rheumatoid arthritis. As such, it is possible that the intra-articular administration of siloxane polymers will exacerbate any preexisting arthritic condition.

Accordingly, it is an object of the present invention to provide methods for the treatment of articular disorders.

It is another object of the present invention to provide methods for the reduction of articular inflammation.

It is yet another object of the present invention to provide methods for the articular administration of therapeutic compounds.

It is still another object of the present invention to provide methods of imaging an articular region providing enhanced contrast.

SUMMARY OF THE INVENTION

These and other objects and advantages are accomplished by the methods of the present invention that, in a broad aspect, provide for the improved diagnosis and treatment of articular disorders. More particularly, the present invention comprises the introduction of fluorocarbons into an articular region for the purpose of treating a disorder, or symptoms thereof including articular inflammation, or delivering a bioactive agent. During the course of therapy, the presence and distribution of the fluorocarbon can be monitored using imaging techniques such as computed tomography, conventional radiography, magnetic resonance imaging and ultrasound. Similarly, high resolution imaging of the articular region, and in particular the synovial cavities, may be achieved using the aforementioned techniques following administration of a neat fluorocarbon liquid to the articular region.

Besides promoting physiological improvements in the articular condition and reduction of pain, the methods of the present invention also act to provide enhanced bioavailability and target specificity for co-introduced bioactive agents as well as improving resolution and clarity of diagnostic images. Unlike prior art compounds introduced into the articular region for management of a disorder, the fluorocarbons of the present invention are safe, nonreactive and extremely biocompatible. Such characteristics, when combined with the efficacious physical properties of the disclosed compounds, allow for the long term therapeutic treatment of articular disorders, or symptoms arising therefrom, without provoking undesirable responses from the patient. Similarly, the enhanced bioavailability and target specificity provided by the present invention prolongs the time a drug may be administered and allows higher doses while lowering the risk of side effects. Additionally, imaging techniques according to the present invention may be used to monitor the progress of the therapy during the normal course of treatments. Other embodiments of the present invention provide for the generation of high resolution images following the administration of a neat fluorocarbon liquid.

In accordance with one aspect of the present invention fluorocarbons may be administered to an articular region to treat an articular disorder or the symptoms thereof. In preferred embodiments the articular disorder is osteoarthritis or rheumatoid arthritis and the fluorocarbon is a liquid fluorocarbon having low water solubility, relatively high density and low surface tension. Upon introduction to the articular region, preferably through intra-articular injection, the fluorocarbon acts to replace or augment the synovial fluid normally found in the joint. Low water solubility acts to retard diffusion out of the synovial space and promotes long residence time at the target site. Low surface tension and an effective coefficient of spreading allows the fluorocarbon to spread evenly over the articular surfaces and provide the desired lubrication and surface uniformity. Similarly, the relatively high density of fluorocarbons provide a natural cushion between opposing surfaces to reduce contact force and attendant pain. In other embodiments, the fluorocarbon may comprise a gel, emulsion or other viscous composition to improve the natural cushioning effect. Moreover, the fluorocarbon may comprise a bioactive agent such as an anti-inflammatory pharmaceutical compound. In preferred embodiments, the method further comprises the step of imaging at least a portion of the articular region following administration of the fluorocarbon. More particularly, as discussed above, the position, amount and condition of the introduced fluorocarbon, as well as the progress of the treatment, may be monitored using conventional imaging techniques during the course of therapy.

Another aspect of the present invention comprises the introduction of a therapeutically effective amount of a fluorocarbon into an articular region reduce inflammation. In particular, the methods of the present invention provide for the introduced fluorocarbon to reduce inflammation without the use of additional bioactive agents. That is, the administered fluorocarbon itself possesses anti-inflammatory properties. Of course, it is contemplated that the fluorocarbon may further comprise a bioactive agent such as steroidal compounds or antibiotics. In particularly preferred embodiments, the selected fluorocarbons may be used to reduce the cellular and molecular events associated with chronic immune cell infiltration which provoke synovial inflammation. As with other aspects of the invention, the form, or state, of the introduced fluorocarbon is not critical and may comprise, for example, a liquid, a gel, an emulsion or the like. Similarly, the present invention may be used without regard as to the cause of the articular inflammation and, further, may be used in any articular region comprising an inflamed joint. In preferred embodiments the fluorocarbon, in any form, will be introduced intra-articularly using an injection. Conversely, the fluorocarbon may be a gel or other preparation that may be introduced using conventional surgical or arthroscopic techniques. Preferably, the method further comprises imaging at least a portion of the articular region following administration of the fluorocarbon to monitor the course of therapy.

Yet another aspect of the present invention involves methods for administering a bioactive agent to an articular region using a bioactive preparation comprising a fluorocarbon and at least one bioactive agent. In these methods, a therapeutically effective amount of the bioactive preparation is introduced to the selected articular region. The selection of the bioactive agent is limited only by the ability to incorporate it in the chosen preparation. Preferred embodiments may incorporate a radioactive element or compound that can act as a radiation synovectomy agent. As with the fluorocarbon in other aspects of the present invention, the bioactive preparation may comprise any one of a number of forms or states including, but not limited to, liquids, solids, gels, sols, suspensions, micelles, emulsions, inverse emulsions and reverse emulsions. Selection of which form to use may be based on factors concerning desired drug delivery profiles, retention times, characteristics of the bioactive agent and type of articular disorder. In a preferred embodiment, the bioactive preparation comprises a plurality of biodegradable polymeric microspheres, associated with the selected bioactive agent, in liquid perfluorocarbon. In other preferred embodiments the biological preparation may be in the form of a gel having a fluorocarbon matrix with a bioactive agent incorporated therein. Such preparations substantially increase bioavailability and target specificity of the bioactive agent while simultaneously reducing undesirable systemic side effects and toxicity. Administration of the bioactive agent may be monitored as described above.

In addition to the aforementioned advantages, the present invention also provides improved methods for imaging an articular region comprising the administration of an effective contrast enhancing amount of a neat liquid fluorocarbon to the selected area. Preferred embodiments comprise the administration of a neat liquid fluorocarbon to the synovial cavities. It will be appreciated that the articular region may be imaged using the same techniques used to monitor the presence or condition of the fluorocarbon during a course of therapy or dosing regimen. In particular, the low water solubility, high density and low surface tension of the neat liquid fluorocarbon serve to provide long lasting, high resolution images of the tissues in the region of interest using magnetic resonance imaging (MRI), computed tomography (CT), conventional radiography and ultrasound. Accordingly, the present invention may be used to obtain enhanced resolution images of the articular region including the joint and the surrounding connective tissue. With respect to CT, conventional radiography and ultrasound, the density and radiopacity of the fluorocarbon contrasts sharply with the water filled tissue. In the case of MRI, the fluorocarbon may be used as a negative contrast agent when imaged using proton weighted MRI or as a positive contrast agent when used in conjunction with $F_{19}$ weighted MRI. Any free flowing, neat liquid fluorocarbon may be used as long as it possesses the necessary contrast enhancing characteristics and any articular region may be imaged using the methods disclosed herein.

Other objects, features and advantages of the present invention will be apparent to those skilled in the art from a consideration of the following detailed description of preferred exemplary embodiments thereof.

DETAILED DESCRIPTION OF THE PREFERRED EMBODIMENT

While the present invention may be embodied in many different forms, disclosed herein are specific illustrative embodiments thereof that exemplify the principles of the invention. It should be emphasized that the invention is not limited to the specific embodiments illustrated.

It will be appreciated that, in a broad aspect, the present invention comprises the administration or introduction of a fluorocarbon into an articular region for a variety of purposes. Among other applications, the methods disclosed herein are particularly useful for treating articular disorders, or the symptoms arising therefrom, due to the excellent lubricating and cushioning properties provided by the selected fluorocarbons. More specifically, preferred embodiments of the invention allow for the replacement or augmentation of natural synovial fluid. This, in turn, provides for the efficient and uniform dispersion of forces placed on the articular region while, at the same time, reducing the forces generated by articular surface opposition. Besides enhancing mobility, the improvement in articular function will result in a reduction of pain and a reduction in the rate of tissue degeneration.

When a fluorocarbon is introduced or administered to an articular region in accordance with the present invention some or all of it preferably adheres the surfaces of the tissue to provide a slick, smooth fluorocarbon coat that minimizes friction. As with natural synovial fluid, it is believed that the introduced fluorocarbon improves the surface homogeneity of the underlying bone or cartilage and, through any one of a number of hydrodynamic mechanisms (depending on the loading of the joint), allows the surfaces to move easily past one another. In addition, the introduced fluorocarbon acts as a cushion to prevent, or at least reduce, the destructive forces generated by contact between opposing surfaces. That is, the introduced fluorocarbon will act to simultaneously separate the surfaces and uniformly dissipate any applied stress or force within the entire articular region. The even dissipation of forces acts to relieve concentrated stress points and, when combined with the fluorocarbon lubrication, retard the further degeneration of the articular tissue. It is also contemplated that the methods of the present invention may also be used to cushion and lubricate prosthetic joints such as those currently employed in artificial hips and knees.

In addition to the unexpected physio-mechanical benefits provided by the present invention, several other advantages are afforded by the disclosed methods. For example, in preferred embodiments the invention may be used to reduce the articular inflammation often associated with joint disorders. More specifically, in selected embodiments fluorocarbons compatible with the present invention may be used to reduce the cellular and molecular events associated with chronic immune cell infiltration, particularly in the synovial cavities, which provoke inflammation. Accordingly, the immunosuppressive aspects of the present invention are preferably employed to reduce synovial inflammation. In particularly preferred embodiments, the treatments are enhanced by the addition of an anti-inflammatory bioactive agent to the fluorocarbon to form a biological preparation which is then administered as provided for herein. As will be discussed further below, the bioactive preparations of the present invention may be used to deliver any compatible bioactive agent to the articular region.

For the purposes of this application, the term "bioactive agent" is defined to mean any pharmaceutical compound or composition, including diagnostic and therapeutic agents as well as live cells, microorganisms and physiologically acceptable gases such as oxygen or nitric oxide, which may be administered to an animal to treat a disorder. Accordingly, a bioactive preparation comprising nutrients, live cartilage producing cells (chondrocytes) and oxygen in a liquid fluorocarbon could be introduced into an articular region according to the present invention. In addition, the contrast enhancing properties of the compatible fluorocarbons allow the tissues of the articular region to be readily delineated during such treatments by imaging at least a portion of the articular region following administration of the fluorocarbon.

The methods of the present invention may be used to treat, alleviate, retard, prevent diagnose, monitor or cure any articular disorder or symptoms arising therefrom. For the purposes of this disclosure the term "articular disorder" shall be held to mean any affliction (congenital, autoimmune or otherwise), injury or disease of the articular region which causes degeneration, pain, reduction in mobility, inflammation or physiological disruption of the articular tissue or connective tissue in the articular region. Specific articular disorders include, but are not limited to, osteoarthritis, rheumatoid arthritis, juvenile arthritis, lupus, scleroderma, chondromalacia patellae, infectious arthritis, bursitis, tendinitis, fibrositis, fibromyositis and polymyositis. Moreover, the methods of the present invention could be used as a prophylactic measure to prevent future damage or degeneration. For example, fluorocarbons could be administered intra-articularly to athletes intermittently throughout their career to minimize the risk of stress related injury or cartilage degeneration.

Those skilled in the art will appreciate that the methods of the present invention are applicable to more than just the joint itself; i.e. more than the point of articulation. By way of example only, the methods of the present invention could be used in the region of the knee to administer fluorocarbon to the subcutaneous infrapatellar bursa (below the kneecap) to lubricate the patellar ligament and reduce inflammation in the surrounding tissue. Accordingly, while the methods of the present invention may be practiced by administering fluorocarbons directly into the articular cavity, it is not limited to such embodiments. Rather, the methods of the present invention are directed to the administration or introduction of the fluorocarbons to the articular region. As defined herein the "articular region" includes the joint itself (the point of articulation), the articular cavity, any ligaments required for joint articulation, any bursa associated with the joint or attendant ligaments and any immediately surrounding tissue. For example, the articular region in the knee extends from the point where the quadriceps femoris tendon attaches to the rectus femoris muscle (below the thigh) to the point where the patellar ligament is affixed to the tibia (above the shin) and comprises all intervening ligaments, cavities, bursa and joints. By way of comparison, "intra-articular" administration (or injection) will be held to mean the introduction of material into any cavity (including bursa and synovial) in proximity to the designated joint.

Furthermore, the present invention is not limited to use in any particular articular region but may be used in conjunction with any selected joint. Exemplary joints that are compatible with the methods of the present invention include, but are not limited to, knee, hip, ankle, shoulder, elbow, tarsal, carpal, interphalangeal and intervertebral. In preferred embodiments the present invention will be used in conjunction with synovial joints. Even more preferably the methods of the present invention are used in conjunction with weight bearing joints such as the hip or the knee. It must be emphasized that, as previously discussed, the present invention provides for the introduction or administration of compatible fluorocarbons to any articular region associated with the aforementioned joints rather than just the point of articulation.

This is especially true with respect to embodiments directed to the reduction of inflammation. As alluded to earlier, the methods of the present invention are particularly beneficial at reducing articular inflammation associated with the synovium. Accordingly, while useful for all articular disorders, the anti-inflammatory aspects of the invention make it very effective for the treatment or prophylaxis of acute inflammation associated with autoimmune articular disorders such as rheumatoid arthritis and ankylosing spondyloarthritis. In such cases, administration of the fluorocarbon to the afflicted joint region may be used to suppress cellular responses such as phagocytosis and molecular activity such as the secretion of cytokines and adhesion molecules. Of course, the anti-inflammatory features disclosed herein are not limited to synovial inflammation. Rather, the methods of the present invention can be used to reduce the inflammation in any tissue (including musculature) associated with the articulation. Administration of the selected fluorocarbon, which in preferred embodiments is perfluorooctylbromide, may be intra-articular, subcutaneous or intramuscular depending on the site of the inflammation to be treated.

Similarly, use of the methods of the present invention to provide high resolution images of an articular region is not limited to administration of the selected fluorocarbon in the synovial cavities. To the contrary the invention may be used to delineate any or all of the tissue desired within the articular region. However, in preferred embodiments, the area to be imaged will comprise at least one synovial cavity.

When used to monitor the course of therapy or determine the placement of fluorocarbon used in such treatments, any form of fluorocarbon (i.e. gels, liquids etc.) may be imaged. However, in order to produce high resolution images of the articular region for the purposes of diagnosis, neat fluorocarbon liquids are used. Generally, the imaging methods of the present invention comprise administering a effective contrast enhancing amount of a neat fluorocarbon liquid to an articular region and imaging the at least a portion of the region. As used herein the term "neat fluorocarbon liquid" shall mean a liquid or liquid preparation that possesses approximately the same flow and spreading characteristics as the liquid in a pure state. Thus, neat fluorocarbon liquids may contain relatively small amounts of additives, including solutes and particulates, as long as the flow characteristics are not impaired. The high density and relatively low surface tension of neat, liquid fluorocarbons allows them to efficiently disperse throughout the selected tissue or cavity providing superior resolution with respect to other forms of fluorocarbon. Preferably the enhanced resolution image will be generated using MRI, radiography (including CT) or ultrasound. The term "effective contrast enhancing amount" shall be held to mean an amount of neat fluorocarbon liquid that improves the definition of the tissue in the imaged area. While this amount may vary, effective ranges for liquid fluorocarbons are between about 0.01 ml and about 20 ml depending on the size of the articular region and type of imaging employed. Preferred regions are on the order of approximately 0.5 ml to approximately 10 ml.

The partially fluorinated or perfluorinated compounds comprising the fluorocarbons of the present invention are typically chosen for their low water solubility, toxicity, high density or viscosity, surface tension and spreading coefficient. Water solubility, density and viscosity are readily determined for any liquid fluorocarbon and may provide an initial screen if the fluorocarbon is to be administered neat. Of course, mixtures of fluorocarbons may be used to provide the desired characteristics. Preferably the fluorocarbons will be capable of delivering therapeutically significant amounts of gases including nitric oxide or oxygen to facilitate treatment. At the same time, it is preferred that the fluorocarbons have vapor pressures sufficiently low to prevent significant liquid loss caused by evaporation during storage or delivery. Lower vapor pressures also promote retention of the fluorocarbon in the articular region where it is introduced and are generally associated with higher viscosity and density. In addition, the ability of the fluorocarbon to spread evenly over the articular surfaces or "wet" the joint is desirable as the uniform distribution will maximize lubrication and dissipation of applied force. Liquid fluorocarbons typically have low surface tension values on the order of 20 dynes/cm and, as they have a relatively high density, spread fairly easy. Accordingly, in this respect almost all liquid fluorocarbons are compatible with the present invention.

Generally, highly fluorinated or perfluorinated compounds having the desired physical properties may be linear, branched or cyclic, saturated or unsaturated fluorinated compounds. Conventional structural derivatives of these fluorocarbons are also contemplated as being within the scope of the present invention. In addition, these totally or partially fluorinated compounds may contain one or more hetero-atoms and/or atoms of bromine or chlorine. As used herein, the term "partially fluorinated" indicates that approximately half or more of the hydrogen atoms in the hydrocarbon oil or derivative thereof have been replaced with fluorine atoms. Preferably, these fluorocarbons comprise from 2 to 16 carbon atoms and include, but are not limited to, linear, cyclic or polycyclic fluorinated alkanes, bis(perfluoroalkyl)alkenes, perfluoroethers, perfluoroamines, perfluoroalkyl bromides and perfluoroalkyl chlorides. With respect to the disclosed methods, the aforementioned compounds may be used either alone or in combination. Moreover, mixtures of the same or different species of fluorocarbons are specifically contemplated as being within the scope of the invention.

In selected embodiments of the invention the fluorinated compound may comprise perfluorooctylbromide, $C_8F_{17}Br$ (PFOB or perflubron). Other preferred alkyl fluorocarbons include perfluoroctane $C_8F_{18}$, perfluorodecane $C_{10}F_{22}$, perfluorodecylbromide $C_{10}F_{21}Br$ (PFDB) and bis(perfluorobutyl) ethene (F-44E). In addition to the these compounds, exemplary fluorocarbons contemplated for use in the present invention generally include halogenated fluorocarbons (i.e. $C_nF_{2n+1}X$, $XC_nF_{2n}X$, where n=2–10, X=Br, Cl or I) and, in particular, 1-bromo-F-butane n-$C_4F_9Br$, 1-bromo-F-hexane (n-$C_6F_{13}Br$), 1-bromo-F-heptane (n-$C_7F_{15}Br$), 1,4-dibromo-F-butane and 1,6-dibromo-F-hexane. Other useful brominated fluorocarbons are disclosed in U.S. Pat. No. 3,975,512 to Long and are incorporated herein by reference. Specific fluorocarbons having chloride substituents, such as perfluorooctyl chloride (n-$C_8F_{17}Cl$), 1,8-dichloro-F-octane (n-$ClC_8F_{16}Cl$), 1,6-dichloro-F-hexane (n-$ClC_6F_{12}Cl$), and 1,4-dichloro-F-butane (n-$ClC_4F_8Cl$) may also be used.

Polycyclic and cyclic fluorocarbons, such as $C_{10}F_{18}$ (F-decalin or perfluorodecalin) are generally useful in the present invention due to their low vapor pressure. Preferred cyclic fluorocarbons include perfluorodecalin and its fluoroalkyl substituents, perfluoroperhydrophenanthrene and its isomers and perfluoroalkyl substituents. Such compounds tend to have a long residence time and provide therapeutic effects in the articular region for an extended period. In this respect, other fluorocarbons which may be useful include, but are not limited to, perfluoro n-butyldecalin, perfluorotetramethylcyclohexane (AP-144), perfluoromethyladamantane, perfluorodimethyladamantane, perfluoro-6,7 H-undec-6-ene, perfluoromethyldecalin, perfluorodimethyl-ethylcyclohexane, perfluorodimethyldecalin, and perfluorodiethyldecalin. Such fluorocarbons, in addition to possessing extended residence times, tend to exhibit desirable viscosity and density characteristics for use in the present invention.

Fluorocarbons, fluorocarbon-hydrocarbon oil compounds and halogenated fluorocarbons containing other linkage groups, such as esters, thioethers and amines are also suitable for use in forming the compositions and bioactive preparations of the present invention. For instance, compounds having the general formula, $C_nF_{2n+1}OC_mF_{2m+1}$, or $C_nF_{2n+1}CH=CHC_mF_{2m+1}$, (as for example $C_4F_9CH=CHC_4F_9$ (F-44E), i-$C_3F_9CH=CHC_6F_{13}$ (F-i36E), and $C_6F_{13}CH=CHC_6F_{13}$ (F-66E where n and m are the same or different and n and m are integers from about 2 to about 12 are compatible with teachings herein. Useful fluorocarbon-hydrocarbon diblock and triblock compounds include those with the general formulas $C_nF_{2n+1}$—$C_mH_{2m+1}$ and $C_nF_{2n+1}$—$C_mH_{2m-1}$, where n=2–12; m=2–16 or $C_pH_{2p+}$—$C_nF_{2n}$—$C_mH_{2m+1}$, where p=1–12, m=1–12 and n=2–12. Preferred compounds of this type include $C_8F_{17}C_2H_5$, $C_6F_{13}C_{10}H_{21}$, $C_8F_{17}C_8H_{17}$, $C_6F_{13}CH=CHC_6H_{13}$ and $C_8F_{17}CH=CHC_{10}H_{21}$. Substituted ethers or polyethers (i.e. $XC_nF_{2n}OC_mF_{2m}X$, $XCFOC_nF_{2n}OCF_2X$, where n and m=1–4, X=Br, Cl or I) and fluorocarbon-hydrocarbon ether diblocks or triblocks (i.e. $C_nF_{2n+1}$—O—$C_mH_{2m+1}$, where n=2–10m=2–6 or $C_pH_{2p+1}$—O—$C_nF_{2n}$—O—$C_mH_{2m+1}$, where p=2–12, m=1–12 and n=2–12) may also used as well as $C_nF_{2n+1}O$—$C_mF_{2m}OC_pH_{2p+1}$, wherein n, m and p are from 1–12. Furthermore, perfluoroalkylated ethers or polyethers may be compatible with the methods of the present invention.

Additional fluorocarbons that may be used in accordance with the teachings herein include perfluorinated amines, such as F-tripropylamine ("FTPA") and F-tributylamine ("FTBA"). F-4-methyloctahydroquinolizine ("FMOQ"), F-N-methyldecahydroisoquinoline ("FMIQ"), F-N-methyldecahydroquinoline ("FHQ"), F-N-cyclohexylpyrrolidine ("FCHP") and F-2-butyltetrahydrofuran ("FC-75"or "FC-77") may also be incorporated. Other contemplated fluorocarbons having nonfluorine substituents, such as, perfluorooctyl hydride, and similar compounds having different numbers of carbon atoms are also contemplated as being within the scope of the invention. Mixtures of any fluorocarbons compatible with the methods disclosed herein are also contemplated for use in the present invention. Further, those skilled in the art will appreciate that other variously modified fluorocarbons are encompassed within the broad definition of "fluorocarbons" and are suitable for use in the present invention.

While some preferred embodiments of the present invention comprise liquid fluorocarbons, it must be emphasized that it is within the scope of the invention to administer or introduce the fluorocarbon to the desiginated articular region in any form. Accordingly, other preferred embodiments of the present invention comprise introducing the fluorocarbon in the form of a liquid, solid, foam, micelle, gel, sol, slurry, dispersion, suspension, emulsion, microemulsion, reverse emulsion and combinations thereof. The selection of which state to use in administering the fluorocarbon will depend, to a large extent, on the type of disorder or symptom being treated and the articular region of interest. For example, in the large articular cavity of the weight bearing knee it may be appropriate to insert a fluorochemical gel or biocompatible sponge soaked with a liquid fluorocarbon to provide extra cushioning. Conversely, in the relatively small, non-weight bearing carpal joints it may be preferred to administer the fluorocarbon as a sol or microemulsion wherein a bioactive agent is suspended as nanometer size particles. In each case, optimization of various aspects of the present invention allows increased bioavailability and maximizes the therapeutic effects of the treatment. For certain embodiments, the methods of the present invention comprise the introduction or administration of a selected, neat fluorocarbon liquid to the designated articular region. In a particularly preferred embodiment, the liquid fluorocarbon is perfluorooctylbromide (PFOB). As alluded to earlier, the neat liquid fluorocarbon may be used to provide beneficial cushioning and lubrication, reduce articular inflammation and act as a contrast agent for real time monitoring of the treatment. The amount of liquid fluorocarbon (or liquid fluorocarbon based preparations such as sols, suspensions, emulsions, etc.) administered is preferably enough to effectively preform the desired function whether it be cushioning, contrast enhancement, anti-inflammation or drug delivery. For mechanical benefits it is contemplated to administer an amount sufficient to replace or augment natural synovial fluid allowing lubrication and cushioning of the afflicted joints. The exact amount administered is generally a function of the joint involved (particularly cavity volume), severity of the articular degradation and other factors related to the disorder. Typically the amount administered may range from approximately 0.01 ml or less for small joints to approximately 10 ml or more for large joints such as the knee. In preferred embodiments, the amount of fluorocarbon administered will range from approximately 0.1 ml to approximately 5 ml.

Those skilled in the art will appreciate that, one major advantage of the present invention is that compounds or materials, including bioactive agents, may be introduced to the articular region in combination with the selected fluorocarbon. In the case of liquid fluorocarbons, selected embodiments comprise the formation of a molecular solution where the bioactive agent or other additive is solubilized in a fluorocarbon carrier. Techniques for forming such solutions are provided by co-pending application U.S. Ser. No. 08/843,468 which is incorporated herein by reference. Other exemplary embodiments of the present invention comprise sols, colloidal dispersions of solid microparticulates on the order of nanometers, or suspensions and dispersions of slightly larger particulates in a fluorocarbon liquid. By increasing the concentration of the suspended particulates, slurries may be obtained. The formation of fluorocarbon based suspensions are well known in the art as evidenced by U.S. Pat. No. 5,496,535 which is incorporated herein by reference. A particularly preferred method of forming sols by driving a bioactive agent or additive out of a fluorocarbon solution is disclosed in co-pending application U.S. Ser. No. 08/482,176 which is also incorporated herein by reference. In forming the aforementioned preparations, those skilled in the art will appreciate that the concentration of the bioactive agents or additives may be adjusted and optimized without undue experimentation to provide a therapeutically effective dosages.

In other embodiments, hydrolytically active (bioerodable) or hydrolytically stable (non-bioerodable) polymeric compounds, typically in the form of microcapsules or microparticulates, may be suspended in the selected fluorocarbon. Preferably, hydrolytically active particlulates will themselves act as a bioactive agent, wetting and lubricating the articular region. It is further contemplated as being within the scope of the invention to associate a bioactive pharmaceutical agent with the polymeric microparticulates or microcapsules used in the dispersion or suspension. The selected polymeric drug delivery vehicles may either be hydrolytically stable or bioerodable depending on the dosing regimen. Preferably, the polymeric microparticulates are sized on the order of approximately 0.02 $\mu$m to 200 $\mu$m, while the microcapsules are sized on the order of approximately 2 $\mu$m to 200 $\mu$m.

Suspensions and sols of non-active or non-bioerodable hydrolytically stable materials such as fluoropolymers (i.e. polytetrafluoroethylene or PTFE), engineering plastics and the like are particularly compatible with the methods of the present invention. In addition to PTFE, other exemplary hydrolytically stable polymers which are suitable for use in the bioactive preparations of the present invention include acrylate, ethylene vinylacetate, polyurethanes, and polysulfones. Such particlates may be used to enhance the beneficial properties of the administered fluorocarbon when coadministered. For example, the inclusion of non-bioerodable nanometer sized particles comprising a hydrolytically inactive polymer in a bioactive preparation may be used to enhance the lubricating characteristics of a cointroduced liquid fluorocarbon. In a particularly preferred embodiment of the present invention, a suspension of PTFE microparticulates in perfluorooctylbromide will be administered to the articular cavity of weight bearing joint. Of course, those skilled in the art will appreciate that the hydrolytically inactive particulates may be associated with a pharmaceutical compound so as to act as a polymeric drug delivery vehicle. Moreover, mixtures of different sizes and/or and different kinds of particulates (i.e. PTFE and acrylate particulates) can be administered in accordance with the teachings herein.

Conversely, exemplary polymers which will erode at the chosen articular site to provide lubrication or wetting of the surface comprise poly(methylvinylether/maleic anhydride), carboxy vinyl polymers, polyfumaric acid/sebacic acid, collagen, gelatin, polyvinyl alcohol, methylcelluloses, polyorthoesters, polyglycolic acid, polylactic acid, polyvinylpyrrolidone, polysebacic acid anhydride, polycarboxyphenoxypropane anhydride, polyterephthalic acid anhydride, and polyphosphazine. Preferred embodiments will comprise poly(methylvinylether/maleic anhydride) particulates or microcapsules. As previously mentioned, particulates and microcapsules comprising such polymers may be associated with pharmaceutical compounds to form polymeric drug delivery vehicles. Such embodiments are especially useful as particulates made from these hydrolytically active polymer provide a long shelf life, do not prematurely erode and are very effective at drug release and lubrication when delivered to the aqueous target environment.

It is also within the scope of the present invention to provide bioactive preparations comprising a mixture of particle sizes or mixtures of microcapsule and microparticulates with varying erosion rates or hydrophobicity profiles. Mixtures of hydrolytically active particles and hydrolytically stable particles are also contemplated. Such combinations can be designed to provide specific drug release profiles, including high initial concentrations or so-called zero order deliveries which may be used to provide combinations of different bioactive agents. However, those skilled in the art will appreciate that particulates or microcapsule prepared from polymers which are hydrolytically labile are especially well suited for use with fluorocarbons of the present invention. In particular, they may be used to form stable preparations having long shelf lives and yet will erode in the aqueous environment of the target site thereby eliminating themselves from the body.

In addition to the liquid fluorocarbon preparations described above, thixotropic preparations may be used in present invention. As is known in the art, a thixotropic composition or compound is one that becomes fluid or less viscous when disturbed or shaken. When the internal shearing force is removed, the viscosity returns to its original "at-rest" value. Natural synovial fluid is a thixotropic material. A suspending aid incorporated in the fluorocarbon is used to impart the desired thixotropic characteristics. Exemplary suspending aids comprise commercially available surfactants, dispersants, suspending agents, and excipients. In preferred embodiments, fluorocarbon-hydrocarbon diblocks may be used. Which suspending aids are used can be determined utilizing routine testing procedures and will, to some extent, be dependent upon the selected pharmaceutical compound, fluorocarbon, form of preparation and method of administration.

Thus, in accordance with the teachings of the present invention, the disclosed preparations may be formed to be relatively viscous or gelatinous when in an undisturbed state yet are capable of liquid like administration or introduction when exposed to the shearing forces associated with a needle or cannula. The high viscosity of the preparation at rest maintains a substantially homogeneous dispersion of a suspended bioactive agent during storage. Yet, when stress is applied to the compositions such as during administration by injection or other methods, the viscosities are greatly reduced, allowing the thixotropic preparations to act as free flowing liquids. In this low viscosity state, the thixotropic preparations behave similarly to a neat liquid fluorocarbon thereby allowing the preparation to spread throughout the articular cavity or other voids. Following administration to the articular target site and removal of the delivery stress, the thixotropic preparations rapidly return to their original higher or "at-rest" viscosities.

Those skilled in the art will appreciate that such thixotropic characteristics may improve the lubricating and cushioning properties of the administered material. In addition to providing a lubricating or wetting function, the increase in viscosity following administration causes the compositions to behave as viscoelastic materials at the target site thereby confining any incorporated bioactive agent and cushioning the articulation. The confinement of the drug provides sharply enhanced bioavailability through a reduction in drug migration or drainage. Moreover, the thixotropic preparations of the present invention can alter the local environment of the target site thereby promoting the adhesion and retention of any incorporated agents on the surface of the tissue. The resultant high localized bioavailability provides increased efficacy and substantially reduces undesirable systemic side effects.

Conversely, the fluorocarbons and bioactive preparations of the present invention may be made dilatant in that the viscosity of the material will increase as the shear rate increases. The increase in viscosity upon the application of dynamic force may be used to increase the cushioning effect of the administered fluorocarbon at the times the force on the point of articulation is the greatest. It will be appreciated that fluorocarbons compatible with the present invention may be made dilatant through established techniques such as providing a concentrated suspension of colloidal particles. These concentrated sols may be formed in the same manner as the previously describe sol preparations. Administration is preferably be effected using a larger bore needle or arthroscopically.

In still other preferred embodiments the administered fluorocarbon or bioactive preparation will be in the form of an emulsion. These emulsions may be thixotropic or dilatant as previously described. Except as otherwise provided or as required by context, the term "emulsion" shall include liposomes, micelles, microemulsions, reverse emulsions, multiple emulsions and gels. As is well know in the art, fluorocarbon emulsions can be prepared using conventional techniques. U.S. Pat. Nos. 4,865,836, 4,927,693 and 4,987,154 all incorporated herein by reference, disclose the formation of fluorocarbon emulsions suitable for use in the present invention. Preferably, one or more surfactant(s), which may be fluorinated or non-fluorinated, are dispersed in an aqueous phase that may contain other additives. Thereafter, fluorocarbons compatible with the teachings herein are provided as, or as a part of, an oily phase which is added to the aqueous phase, followed by dispersion of the whole utilizing conventional techniques. Of course those skilled in the art will appreciate that other, equally effective techniques may be used to form emulsions compatible with the present invention. In other embodiments reverse emulsions, where the continuous phase is the oil phase and the discontinuous or dispersed phase is the aqueous or polar liquid phase, may be administered to the articular region. Reverse emulsions, micelles, microemulsions and multiple emulsions comprising fluorocarbons are described in co-pending application U.S. Ser. No. 08/487,612 which is incorporated herein by reference. Similarly, hydrocarbon-in-fluorocarbon emulsions suitable for use in the present invention are described in co-pending application U.S. Ser. No. 08/572,859 that is also incorporated herein by reference. Of course bioactive agents may be combined with the emulsions to provide bioactive emulsion preparations in accordance with the teachings herein.

In those cases where the emulsion comprises an aqueous phase, additives may be included to achieve certain, desired effects, such as particle size stability, osmolarity, thermal stability, and the like. Therefore, additives such as mineral salts, buffers, osmotic agents, oncotic agents, anti-oxidants such as alpha-tocopherol, and pharmaceutical and/or nutritive products, chosen according to the application of the emulsion are contemplated, as well as other agents. Hydrophilic bioactive agents may also be added to the aqueous phase of articular compatible emulsions.

Similarly, a variety of surfactants, including fluorinated surfactants may be used to form emulsions in accordance with the present invention. Like additives in the aqueous phase, surfactants are chosen according to the desired properties of the emulsion. Examples of suitable surfactants for use in the present invention include lecithins, polyoxyethylene-polyoxypropylene copolymers, sorbitan polyoxy-ethylenes, phospholipids such as egg-yolk, soya or synthetic lipids, perfluoroalkyl phospholipids and the other synthetic perfluoroalkyl surfactants.

Preferred concentrations of components for selected emulsions or gels that are compatible with the present invention are generally as follows:

from 10 to 120% in weight/volume of an oily phase,
from 0.1 to 10% in weight/volume of surfactant(s), and
the aqueous phase making up the balance.

Microemulsions may be preferably prepared with the following ratios:

from 10 to 120% in weight/volume of an oily phase,
from 3 to 30% in weight/volume of surfactant(s), and
the aqueous phase making up the balance.

In general, fluorocarbon gels will comprise a higher concentration of the continuous oil phase to provide the desired viscosity. For example, fluorocarbon gels suitable for use in the present invention contain up to 98% w/v of the fluorocarbon APF 260, (Air Products) 0.2% w/v F-alkylamidopropyl dimethylamine oxide (surfactant) and distilled water to 100%. As with the other emulsions and liquid fluorocarbons, the gels may comprise bioactive agents or other additives as previously described.

The route of administration may be selected depending on the form of the fluorocarbon or bioactive preparation to be introduced to the articular region. For example, in the case of flowing materials such as liquids, emulsions or gel precursors administration by injection, including intra-articular, is preferred. In this respect, it is contemplated that gel components may be combined and injected in a fluid state and allowed to gel in the target area. It must be reiterated that, whatever the form of the fluorocarbon or bioactive preparation, introduction or administration of the material is not limited to the point of articulation or specific cavities but rather may be anywhere in the articular region. For example, a liquid fluorocarbon may be injected into the tissue or fat immediately adjacent to a tendon to reduce inflammation and provide beneficial lubrication. Similarly, a bioactive preparation may be injected directly into a single bursa in contact with a ligament to deliver oxygen and a pharmaceutical composition to that localized area. In contrast, relatively large volumes of a thixotropic fluorocarbon preparation may be introduced into each of the synovial cavities in and around the selected joint to provide mechanical cushioning and lubrication to relieve the symptoms of osteoarthritis.

Nor is the form of administration limited to specific methods. Any manner of introducing or administering the fluorocarbon or bioactive preparation to the articular region is within the scope of the invention. For example, a preformed fluorocarbon gel carrying high concentrations of oxygen may be introduced to the articular cavity of the knee through conventional surgical techniques. In this vein a solid biocompatible material, such as a lipophilic sponge, may be soaked with a selected fluorocarbon and surgically positioned in the joint to cushion the articular surfaces. Similarly, a dilatant sol comprising prednisone may be administered to the articular cavity of the elbow using arthroscopic techniques well known in the art. It will therefore be appreciated that any techniques for introducing liquids or solids to the appropriate areas of the body are within the scope of the invention.

The bioactive preparations of the present invention are capable of delivering any desired bioactive agent that may be incorporated in the introduced material. Due to the use of fluorocarbons the present invention is particularly useful in delivering lipophilic agents which otherwise exhibit poor bioavailability. In preferred embodiments, lipophilic agents are combined with the chosen fluorocarbon to form a molecular solution or with the disperse phase in conventional fluorocarbon emulsions either prior to or after formation. Similarly, the fluorophilic agent may be combined with a fluorocarbon to provide a sol or suspension. Conversely, water soluble bioactive agents may be combined with the continuous phase of regular emulsions or the disperse phase in reverse emulsions. As previously defmed, the term "bioactive agent" means any pharmaceutical compound or composition, including diagnostic and therapeutic agents, living cells or microorganisms and physiologically acceptable gases such as oxygen or nitric oxide, which may be administered to an animal to treat a disorder. Preferred bioactive agents include hydrophilic drugs with solubility in water and lipophilic agents.

As discussed, any bioactive agent that may be incorporated in the bioactive preparations of the present invention may be used. Yet, some indication as to the general ability of an individual bioactive agent to be incorporated in a fluorocarbon (and in what form) may be derived from the measured value of its lipophilicity. The convention is to measure and report the lipophilicity of a bioactive agent using the log of the octanol/water partition coefficient (Log $P_{o/w}$). In this system increasing lipophilicity corresponds to higher Log $P_{o/w}$ values. Preferably, lipophilic bioactive agents incorporated in the present invention will have a Log $P_{o/w}$ greater than about 0.5. More preferably the lipophilic bioactive agents will have a Log $P_{o/w}$ greater than about 2.0. As those skilled in the art will appreciate, values such as these indicate that a compound has limited solubility in an aqueous environment and are difficult to deliver using conventional vehicles. The octanol/water partition coefficients of several exemplary lipophilic bioactive agents compatible with the teachings of the present invention, are reproduced below in Table 1.

TABLE 1

Octanol/water partition coefficients (Po/w) of various drugs

| Drug Substance | $P_{o/w}$ | Log $P_{o/w}$ |
|---|---|---|
| C-anthracene[1] | $3.16 \times 10^4$ | 4.5 |
| C-bunolol[1] | $2.51 \times 10^2$ | 2.4 |
| C-cimetidine[1] | 2.51 | 0.4 |
| C-hexamethylene lauramide[1] | $2.00 \times 10^7$ | 7.3 |
| C-padimate-o[1] | $3.98 \times 10^6$ | 6.6 |
| C-progesterone[1] | $7.9 \times 10^3$ | 3.9 |
| C-testosterone[1] | $2.00 \times 10^3$ | 3.3 |
| H-clonidine[1] | 25.1 | 1.4 |
| H-diethylstilbesterol[1] | $1.26 \times 10^5$ | 5.1 |
| H-fluorometholone[1] | $1.26 \times 10^2$ | 2.1 |
| H-parsol 1789[1] | $5.0 \times 10^6$ | 6.7 |
| valeryl acyclovir[2] | 2.01 | 0.30[a] |
| hexanoyl acyclovir[2] | 8.58 | 0.93[a] |
| lidocaine[3] | 2.88 | 0.46 |
| bupivacaine[3] | 28.2 | 1.45 |
| tetracaine[3] | 79.4 | 1.90 |
| halothane[4] | $2.00 \times 10^2$ | 2.30 |
| ampicillin[4] | 11.5 | 1.06 |
| oxazepam[4] | $1.78 \times 10^2$ | 2.25 |
| pentazocin[5] | 150 | 2.18[a] |
| nitrazepam[5] | 162 | 2.21[a] |
| haloperidol[5] | 485 | 2.69[a] |
| biperiden[5] | 678 | 2.83[a] |
| diazepam[5] | 970 | 2.99[a] |
| promethazine[5] | $1.27 \times 10^3$ | 3.10[a] |
| trihexyphenidyl[5] | $1.47 \times 10^3$ | 3.17[a] |
| chiorpromazine[5] | $1.90 \times 10^3$ | 3.28[a] |
| clotiazepam[5] | $3.06 \times 10^3$ | 3.49[a] |
| clomipramine[5] | $3.80 \times 10^3$ | 3.58[a] |

[1]Tang-Liu, D. D. -S., Richman, J. B. and Liu, S. S., J. Ocul. Pharmac., 1992, 8, 267.
[2]Hughes, P. M. and Mitra, A. K., J. Ocul. Pharmac., 1993, 9, 299.
[3]Hageluken, A., Grunbaum, L., Numberg, B., Harhammer, R., Schunack, W. and Seifert, R., Biochem. Pharmac., 1994, 47, 1789.
[4]Moriguchi, I., Hirono, S., Liu, Q., Nakagome, I. and Matsuchita, Y., Chem. Pharm. Bull., 1992, 40, 127.
[5]Yokogawa, K., Nakashima, E., Ishizaki, J., Maeda, H., Nagano, T. and Ichimura, F., Pharm. Res. 1990, 7, 691.
[a]in octanol/Ph 7.4 isotonic phosphate buffer at 37° C.

Preferably, the bioactive preparations of the present invention incorporates less than about 50% w/v of a therapeutic or diagnostic agent. Typically, diagnostics agents will be incorporated at higher concentrations. The precise amount of bioactive agent incorporated in the preparations of the present invention is dependent upon the agent of choice, the required dose, and the form of the drug actually used for incorporation. Those skilled in the art will appreciated that such determinations may be using well-known pharmacological techniques in combination with the teachings of the present invention.

Preferred bioactive agents comprise hydrophilic and lipophilic anti-inflammatories, antibiotics, antivirals, antihistimics, anti-neoplastics, anesthetics, enzymes, active principals, nucleic acids, genetic material, viral vectors, immunoactive agents, imaging agents, immunosuppressive agents, peptides, proteins, physiological gases and combinations thereof.

Further exemplary embodiments of the present invention comprise anti-inflammatory agents such as the glucocorticosteroids (i.e. cortisone, prednisone, prednisolone, dexamethasone, betamethasone, beclomethasone diprionate, triamcinolone acetonide, flunisolide) and non-steroidal anti-inflammatory drugs, xanthines (i.e. theophylline, caffeine), chemotherapeutics (i.e. cyclophosphamide, lomustine, methotrexate, cisplatin, carboxy platin, taxane derivatives), antibiotics (i.e. aminoglycosides, penicillins, cephalosporins, macolides, quinolones, tetracyclines, chloramphenicol), $B_2$-agonists (i.e. adrenaline, isoprenaline, salmeterol, salbutamol, terbutaline, formoterol) and surfactants. Still other exemplary embodiments include α/β adrenergic blockers (i.e. Normodyne, Trandate), calcium channel blockers, inotropic agents, anesthetics (i.e. morphine).

Most preferred agents include glucocorticosteroids, non-steroidal anti-inflammatory drugs, taxane derivatives (i.e. Taxol, Taxotere) and the base forms of drugs typically administered as the salt derivative (i.e. Gentamicin, Ciprofloxacin). In accordance with the present invention, those skilled in the art will appreciate that various forms (different pharmaceutically acceptable salts, prodrugs, etc.) of these compounds may be used to modify the therapeutic index of the bioactive agents. Accordingly, the foregoing lists of bioactive agents are exemplary only and not intended to be limiting. As is well known, the proper amount of bioactive agent and the timing of the dosages may be determined for the preparations in accordance with already-existing information and without undue experimentation.

As alluded to earlier, the selected bioactive agent may be a radioactive compound. Such agents could be incorporated in bioactive preparations useful for performing radiation synovectomy. Conventional synovectomy is surgical removal of the damaged synovial membrane, typically to treat sufferers of rheumatoid arthritis, which is painful and often ineffective. Radiation synovectomy is ablation of the damaged synovial membrane using radioactive material injected into the afflicted area. Although this method has proven effective, it suffers from the fact that aqueous radioactive material rapidly leaks from the synovial cavities into the interstitial spaces and can become concentrated in the lymph nodes providing unacceptable radiation dosages to sites distant from the afflicted area. The present invention overcomes these drawbacks through hydrophilic retention in the synovial space and prolonged target specificity. Accordingly, alpha and/or beta emitters could be used to form bioactive preparations, preferably thixotropic, as described herein and introduced into the desired synovial cavity. Destruction of the inflamed synovium is effected without surgery or the systemic side effects and lymphatic concentration presently observed.

It will further be appreciated by those skilled in the art that the fluorocarbons and bioactive preparations of the present invention may be sterilized, for example, by heat, irradiation, ultrafiltration or combinations of any of these or equivalent techniques.

The fluorocarbons and high bioavailability bioactive preparations of the present invention may advantageously be supplied to the physician in a sterile prepackaged form. More particularly, the formulations may be supplied as stable, preformed emulsions, suspensions gels, etc., ready for administration or as separate, ready to mix components. Typically, when supplied as components the fluorocarbon, optionally incorporating a bioactive agent, will be packaged separately. This bioactive dispersion or suspension could then be mixed, generally by the physician or in a hospital lab, with a sterile polar liquid phase (i.e. water) to form an emulsion, gel reverse emulsion, etc. of the present invention. In such cases, the polar liquid phase could be supplied either by the manufacturer or the final user.

Finally it will be appreciated that the methods of the present invention are not limited to use in human beings and may advantageously be used on any organism possessing articulations. For instance, the methods disclosed herein may be used on race horses to reduce inflammation and cushion the knee and ankle joints. Similarly, other farm livestock and domestic animals may benefit from the veterinary applications of the disclosed methods.

The following nonlimiting examples of various formulations of the present invention illustrate exemplary methods for the their formation and resultant characteristics.

EXAMPLE 1

Preparation of a Suspension of Prednisone in a Fluorochemical Suitable for Administration to an Articular Region To further demonstrate the benefits of the present invention a bioactive preparation was provided in the form of a sol containing prednisone, a synthetic steroid commonly used for the treatment of rheumatoid arthritis. Three milliliters of the following fluorochemical continuous suspension was prepared:

Composition 1

0.38%, w/v, Prednisone (Sigma Chemical Co.) was dissolved into a solution composed of 1,4-dibromo-F-butane (50%, v/v; Exfluor, Austin, Tex.) and NF grade ethyl alcohol (50%, v/v; Spectrum Chemical Co).

Fluorochemical Diluent

Perfluorooctylbromide (Atochem, France)

An aliquot of composition 1 (60 $\mu$L) was injected with a syringe into a sample of perfluorooctylbromide (PFOB; 3 mL) contained in a 12×100 mm test tube. The tube was capped and the contents gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 60±42 nm.

EXAMPLE 2

Administration of a Suspension of Prednisone to the Articular Region of a Patient A patient suffering from advanced osteoarthritis in a hip joint is treated using the methods of the present invention. The patient is positioned to facilitate gravitational dispersion of the free flowing bioactive preparation. A small amount (on the order of a few milliliters) of the bioactive preparation described in Example 1 is injected into the articular cavity using a standard syringe and needle. During administration the dispersion of the bioactive preparation in the cavity is monitored by imaging the articular region using conventional radiography. Upon observing complete dissemination of the bioactive preparation throughout the articular region the injection of material is halted and the needle withdrawn. The small particle size and even dispersion of the prednisone in the fluorocarbon serve to optimize the anti-inflammatory and immunosuppressive effects of the bioactive preparation. The process is repeated on the order of once a month for a period of six months in order to maintain an effective therapeutic amount of the bioactive preparation within the articular cavity.

EXAMPLE 3

Preparation of a Suspension of Paclitaxel In Fluorochemical Suitable for Administration to an Articular Region The versatility of the present invention with respect to the types of articular disorder that may be treated is shown by the formation of a bioactive preparation comprising paclitaxel, a potent anti-neoplastic agent. Three milliliters of the following fluorochemical continuous suspension was prepared:

Composition 1

0.40% w/v of paclitaxel (Sigma Chemical Co.) was dissolved into a solution composed of 1,4-dibromo-F-butane (50%, v/v; Exfluor, Austin, Tex.) and NF grade ethyl alcohol (50%, v/v; Spectrum Chemical Co.).

Fluorochemical Diluent

Perfluorooctylbromide (Atochem, France).

An aliquot of composition 1 (60 µL) was injected with a syringe into a sample of perfluorooctylbromide (PFOB; 3 mL) contained in a 12×100 mm test tube. The tube was capped and the contents gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 50±32 nm.

EXAMPLE 4

Administration of a Suspension of Paclitaxel In Fluorochemical to an Articular Region of a Patient Suffering From Fibrosarcoma The paclitaxel sol formed in Example 3 is used to deliver the drug to bursa of a hip of a patient suffering from fibrosarcoma. Treatment is initiated by imaging the afflicted articular region using MRI to locate a bursa adjacent to and in contact with the tumor. Following preparation and positioning of the patient a needle is used to puncture the bursa. A small amount (on the order of 1 ml) of the bioactive preparation is injected into the bursa while the procedure is monitored. The needle is then withdrawn. This procedure is repeated once a week, alone or in combination with other therapy, until the tumor is eliminated.

It will be appreciated that the bioactive preparation provides the high bioavailability and target specificity necessary to aggressively treat the tumor while reducing the inherent toxicity of the paclitaxel. This allows higher doses of the drug to be administered thereby shortening the duration of the treatment and reducing patient discomfort.

EXAMPLE 5

Preparation Of A Submicron Sized Ciprofloxacin Suspension in Fluorochemicals Suitable for Administration to an Articular Region An antibacterial bioactive preparation comprising ciprofloxacin, suitable for use in the present invention, was formed. Specifically, three milliliters of the following submicron sized fluorochemical suspension was prepared:

Composition 1

0.35, w/v, Cyprofloxaxin HCl (Miles, Inc.) was dissolved in the presence of 100 mg $Na_2Co_3$ (NF Grade, Spectrum Chemical) into a solution composed of 1,4-dibromo-F-butane (50%, v/v; Exfluor, Austin, Tex.) and NF grade ethyl alcohol (50%, v/v; Spectrum Chemical Co).

Fluorochemical Diluent

Perfluorooctylbromide (Atochem, France)

An aliquot of composition 1 (90 µL) was injected with a syringe into a sample of perfluorooctylbromide (PFOB; 3 mL) contained in a 12×100 mm test tube. The tube was capped and gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 55±47 nm.

EXAMPLE 6

Administration of a Submicron Sized Ciprofloxacin Suspension in Fluorochemicals to a Patient Suffering From a Bacterial Infection of an Articular Region In accordance with the teachings herein, the suspension of Example 5 is adjusted to provide the proper dosing and administered by intra-articular injection to a patient with a bacterial infection of the synovial cavities in the ankle. Small volumes of approximately 0.5 ml or less are used with treatments repeated until the infection is eliminated.

The even dispersion of the drug and localized bioavailability ensures the bactericidal efficacy of the preparation while the fluorocarbon reduces the bacterial induced inflammation of the synovium and provides lubrication and cushioning to reduce the discomfort of the patient.

EXAMPLE 7

Preparation of a Gentamicin Sulfate Reverse Emulsion Suitable for Administration to an Articular Region To demonstrate that a variety of fluorocarbon forms may be used in accordance with the present invention and that relatively hydrophilic drugs may be delivered effectively, three mL of the following reverse emulsion formulation containing Gentamicin was prepared.

0.051% w/v Gentamicin sulfate (Sigma)

1.0% w/v 1,2 Dioleoylphosphatidylethanolamine (DOPE; Avanti)

0.21% w/v Di-olein (Nu-Chek Prep, Elysian, Minn.)

90% v/v α, ω-Dibromo-F-butane (Exfluor)

0.09% sodium chloride (Sigma)

0.09% calcium chloride (Sigma)

10% v/v water for injection

Dioleoylphosphatidylethanolamine (100 mg) was dispersed in α, ω-dibromo-F-butane (DBFB; 18 g) with a Vibracell™ sonicator (Sonics Materials, 30 mm o.d. titanium probe) at a power of 100 watts for approximately 1 minute (T=5°–10° C.). An electrolyte solution (1.0 mL, 10% v/v) was then added dropwise during sonication. After the addition was complete, the reverse emulsion was sonicated for a total of not less than 10 minutes. The electrolyte solution contained 0.9% w/v NaCl and 0.9% w/v $CaCl_2$ ($2H_2O$). A milky water-in-fluorocarbon emulsion was obtained. Particle size of the emulsions was analyzed via laser light scattering on a Nicomp 270 photon correlation spectrometer (Pacific Scientific). Analysis was by the method of cumulants. Each emulsion sample was first diluted with n-octane since the refractive indices of the continuous and dispersed phases are nearly equal. The resulting reverse water-in-fluorocarbon emulsion had a mean droplet size of about 145±70 nm. The reverse character of the emulsion was established by conductivity and by stability after dilution with a hydrocarbon oil (i.e., n-octane).

EXAMPLE 8

Administration of a Gentamicin Sulfate Reverse Emulsion to an Articular Region of a Patient Suffering From a Bacterial Infection In keeping with the teachings herein the reverse emulsion of Example 7 is administered to the elbow of a patient suffering from an articular bacterial infection. The elbow is oriented to facilitate dispersion of the bioactive preparation and imaged using ultrasound. A small amount (on the order of 1 ml) of the bioactive emulsion is administered to the articular cavity using a conventional syringe. Alternatively, if the elbow was infected due to trauma or following surgery, administration may take place directly, i.e. by placing the reverse emulsion directly on the exposed articular tissue. In both cases ultrasound may be used to confirm the presence and dispersion of the bioactive emulsion. The method is repeated once after a period of three days to ensure the infection is eradicated.

EXAMPLE 9

Preparation of a Hydrocarbon-in-Fluorocarbon Emulsion Suitable for Administration to an Articular Region To further demonstrate the diversity of the present invention, a hydrocarbon-in-fluorocarbon emulsion suitable for administration to provide articular cushioning and lubrication was prepared.

An aliquot of F-Octanes (8.82 g) was titrated with n-hexane until phase separation occurred (1.70 mL). This was indicated by the formation of a cloudy white mixture which upon sitting quickly separated into two clear, colorless phases separated by a distinct interface. 1-(F-octyl) hexadecane (0.68 g) was then added to the mixture and the solution mixed to obtain a clear, colorless single liquid phase. The titration with hexane was continued until the solution took on a bluish tint characteristic of microemulsions containing very small droplets (diameter$\leq$100 nm). The system was allowed to equilibrate at 20° C. No indication of phase separation was observed over a 10 day period and the formation of this phase was reversible. The particle size was measured by photon correlation spectroscopy (PCS; Nicomp Model 270 Submicron Particle Sizer) and the number weighted mean diameter determined to be 14.5 nm and relatively monodisperse (standard deviation= ±2.7 nm). The fluorocarbon continuous nature of this system was confirmed by the fact that the solution could be diluted with F-octanes without phase separation. When an excess of hydrocarbon (ca 50%, v/v) was added the solution separated into two roughly equivolume clear, colorless liquids with a distinct interface between them. These characteristics were consistent with the formation of 1-(F-octyl)hexadecane micelles into which the hydrocarbon oil had been solubilized.

EXAMPLE 10

Administration of a Hydrocarbon-in-Fluorocarbon Emulsion to the Articular Region of a Patient Suffering From Rheumatoid Arthritis an Articular Region A patient suffering from rheumatoid arthritis in the hips is treated in accordance with the methods of the present invention. Initially, the patient is oriented in a position to facilitate dispersion of the fluorocarbon throughout the articular cavity. The articular region is imaged using conventional radiography. Ten milliliters of the emulsion of Example 9 is prepared in a conventional syringe arrangement. The tip of the needle is positioned within the articular cavity of the hip joint and injection of the emulsion is effected. Images of the area of interest are monitored to determine the spread of the bioactive preparation within the cavity. An effective therapeutic amount of emulsion, enough to augment the natural synovial fluid, is injected. The needle is then removed from the patient. The procedure may be repeated as needed (for example, once a month) for as long as necessary.

It will be appreciated that hydrophobic drugs, such as steroids, could be solubilized into the hydrocarbon droplets prior to forming the emulsion. The administered emulsion will provide the desired mechanical support as previously described in addition to reducing the synovial inflammation.

EXAMPLE 11

Preparation of a Drug-Containing Hydrocarbon-in-Fluorocarbon Emulsion Suitable for Administration to an Articular Region To further demonstrate the ability of the present invention to effectively deliver a wide spectrum of bioactive agents to an articular region, the following bioactive preparation was formed:

An aliquot of F-Octanes (8.82 g) was titrated with methyl salicylate (a bioactive agent) until phase separation occurred (10–20 $\mu$L). 1(F-hexyl)tetradecane (1.04 g) was then added to the mixture and the solution mixed to obtain a clear, colorless single liquid phase. The titration with methyl salicylate was continued until the solution took on a bluish tint characteristic of microemulsions containing very small droplets (diameter$\leq$100 nm). The system was allowed to equilibrate at 20° C. and the particle size measured by photon correlation spectroscopy (PCS; Nicomp Model 270 Submicron Particle Sizer). The number weighted mean diameter was measured to be 9.0 nm (standard deviation= ±0.8 nm). These characteristics were consistent with the solubilization of methyl salicylate by 1 (F-hexyl)tetradecane (F6H14) micelles.

EXAMPLE 12

Administration of a Drug-Containing Hydrocarbon-in-Fluorocarbon Emulsion to an Articular Region A patient is treated to reduce the pain and inflammation associated with a hyperextended knee. The articular region is imaged using conventional radiography to locate the synovial cavity nearest the site of inflammation. Approximately half a milliliter of the hydrocarbon-in-fluorocarbon bioactive emulsion described in Example 11 is administered to the suprapatellar synovial bursa of a patient. Insertion of the needle and introduction of the bioactive preparation is monitored through the real time radiographic images. The incorporated methyl salicylate acts to reduce the pain associated with a hyperextended knee while, at the same time, the fluorocarbon emulsion acts to reduce the inflammation in the area of the kneecap and lubricates the quadriceps femoris tendon.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A method for cushioning or lubricating a joint in a patient in need thereof comprising the step of administering a therapeutically effective cushioning or lubricating amount of a fluorocarbon to at least one articular region.

2. The method of claim 1 wherein the administered fluorocarbon is in a form selected from the group consisting of liquids, solids, foams, micelles, gels, sols, slurries, dispersions, suspensions, emulsions, microemulsions, reverse emulsions and combinations thereof.

3. The method of claim 2 wherein said fluorocarbon comprises a suspension and said fluorocarbon suspension comprises a liquid fluorocarbon continuous phase having suspended therein a plurality of particulates selected from the group consisting of solid fluorocarbon particulates and polymeric drug delivery vehicles.

4. The method of claim 1 wherein said patient is suffering from an articular disorder selected from the group consisting of osteoarthritis rheumatoid arthritis, juvenile arthritis, lupus, scleroderma, chondromalacia patellae, infectious arthritis, bursitis, tendinitis, fibrositis, fibromyositis and polymyositis.

5. The method of claim 1 wherein said articular region comprises a joint selected from the group consisting of knee, hip, ankle, shoulder, elbow, tarsal, carpal, interphalangeal and intervertebral.

6. The method of claim 1 wherein said articular region comprises a synovial cavity and said flurocarbon is introduced into said synovial cavity.

7. The method of claim 1 wherein said fluorocarbon is selected from the group consisting of fluorinated alkanes, fluorinated cyclic compounds, halogenated fluorocarbons, fluorinated alkenes, fluorinated ethers, fluorinated polyethers, fluorinated amines, fluorinated hydrides and derivatives thereof.

8. The method of claim 1 wherein said fluorocarbon further comprises a bioactive agent.

9. The method of claim 8 wherein said bioactive agent is selected from the group consisting of antibiotics, antivirals, anti-inflammatories, antineoplastics, anesthetics, enzymes, active principals, nucleic acids, genetic material, viral vectors, immunoactive agents, imaging agents, immunosuppressive agents, peptides, proteins, physiological gases and combinations thereof.

10. The method of claim 8 wherein said bioactive agent is associated with a polymeric drug delivery vehicle.

11. The method of claim 8 wherein said bioactive agent comprises a radioactive compound.

12. The method of claim 1 wherein said fluorocarbon comprises a liquid fluorocarbon and said liquid fluorocarbon is administered by intra-articular injection.

13. The method of claim 1 wherein said articular region comprises a prosthetic joint.

14. The method of claim 1 further comprising the step of imaging at least a portion of the articular region following administration of said fluorocarbon.

15. The method of claim 14 wherein said imaging step comprises a imaging technique selected from the group consisting of magnetic resonance imaging, conventional radiography, computed tomography and ultrasound.

16. The method of claim 14 wherein the fluorocarbon is administered into at least one synovial cavity.

17. A method for reducing articular inflammation in a joint comprising the step of introducing a therapeutically effective inflammation reducing amount of a fluorocarbon into at least one synovial cavity associated with said joint.

18. The method of claim 17 wherein said fluorocarbon is in a form selected from the group consisting of liquids, solids, foams, micelles, gels, sols, slurries, dispersions, suspensions, emulsions, microemulsions, reverse emulsions and combinations thereof.

19. The method of claim 17 wherein the articular inflammation is the result of an articular disorder selected from the group consisting of osteoarthritis, rheumatoid arthritis, juvenile arthritis, lupus, scleroderma, chondromalacia patellae, infectious arthritis, bursitis, tendinitis, fibrositis fibromyositis and polymyositis.

20. The method of claim 17 wherein said joint is selected from the group consisting of knee, hip, ankle, shoulder, elbow, tarsal, carpal, interphalangeal and intervertebral.

21. The method of claim 17 wherein said fluorocarbon is selected from the group consisting of fluorinated alkanes, fluorinated cyclic compounds, halogenated fluorocarbons, fluorinated alkenes, fluorinated ethers, fluorinated polyethers, fluorinated amines, fluorinated hydrides and derivatives thereof.

22. The method of claim 17 wherein said fluorocarbon further comprises a bioactive agent.

23. The method of claim 22 wherein said bioactive agent is selected from the group consisting of antibiotics, antivirals, anti-inflammatories, anti-neoplastics, anesthetics, enzymes, active principals, nucleic acids, genetic material, viral vectors, immunoactive agents, imaging agents, immunosuppressive agents, peptides, proteins, physiological gases and combinations thereof.

24. The method of claim 17 wherein said fluorocarbon comprises a liquid fluorocarbon and said liquid fluorocarbon is administered by intra-articular injection.

25. The method of claim 17 further comprising the step of imaging at least a portion of said joint following administration of said fluorocarbon.

26. A method for replacing or augmenting synovial fluid in a joint in a patient in need thereof comprising the step of administering a therapeutically effective lubricating amount of a fluorocarbon to at least one synovial cavity wherein said fluorocarbon cushions or lubricates said joint.

27. The method of claim 26 wherein the administered flurocarbon is in a form selected from the group consisting of liquids, solids, foams, micelles, gels, sols, slurries, dispersions, suspensions, emulsions, microemulsions, reverse emulsions and combinations thereof.

28. The method of claim 26 wherein said fluorocarbon comprises a suspension and said fluorocarbon suspension comprises a liquid fluorocarbon continuous phase having suspended therein a plurality of particulates selected from the group consisting of solid fluorocarbon particulates and polymeric drug delivery vehicles.

29. The method of claim 26 wherein said patient is affected by an articular disorder selected from the group consisting of osteorthritis, rheumatoid arthritis, juvenile arthritis, lupus, scleroderma, chondromalacia patellae, infectious, arthritis, bursitis, tendinitis, fibrositis, fibromyositis and polymyositis.

30. The method of claim 26 wherein said synovial cavity is associated with a joint selected from the group consisting of knee, hip, ankle, shoulder, elbow, tarsal, carpal, interphalangeal and intervertebral.

31. The method of claim 26 wherein said fluorocarbon is selected from the group consisting of fluorinated alkanes, fluorinated cyclic compounds, halogenated fluorocarbons, fluorinated alkenes, fluorinated ethers, fluorinated polyethers, fluorinated amines, fluorinated hydrides and derivatives thereof.

32. The method of claim 26 wherein said fluorocarbon further comprises a bioactive agent.

33. The method of claim 32 wherein said bioactive agent is selected from the group consisting of antibiotics, antivirals, anti-inflammatories, antineoplastics, anesthetics, enzymes, active principals, nucleic acids, genetic material, viral vectors, immunoactive agents, imaging agents, immunosuppressive agents, peptides, proteins, physiological gases and combinations thereof.

34. The method of claim 33 wherein said bioactive agent is associated with a polymeric drug delivery vehicle.

35. The method of claim 32 wherein said bioactive agent comprises a radioactive compound.

36. A method for reducing the rate of tissue degeneration in an articular region comprising:

introducing an effective lubricating amount of a composition comprising at least one fluorocarbon into at least one synovial cavity in said articular region whereby the rate of degeneration of said tissue is retarded.

37. The method of claim 36 wherein the administered fluorocarbon is in a form selected from the group consisting of liquids, solids, foams, micelles, gels, sols, slurries, dispersions, suspensions, emulsions, microemulsions, reverse emulsions and combinations thereof.

38. The method of claim 36 wherein said fluorocarbon comprises a suspension and said fluorocarbon suspension comprises a liquid fluorocarbon continuous phase having suspended therein a plurality of particulates selected from the group consisting of solid fluorocarbon particulates and polymeric drug delivery vehicles.

39. The method of claim 36 wherein said tissue degeneration is associated with an articular disorder selected from the group consisting of osteoarthritis, rheumatoid arthritis, juvenile arthritis, lupus, scleroderma, chondromalacia patellae, infectious arthritis, bursitis, tendinitis, fibrositis, fibromyositis and polymyositis.

40. The method of claim 36 wherein said articular region comprises a joint selected from the group consisting of knee, hip, ankle, shoulder, elbow, tarsal, carpal, interphalangeal and intervertebral.

41. The method of claim 36 wherein said fluorocarbon is selected from the group consisting of fluorinated alkanes, fluorinated cyclic compounds, halogenated fluorocarbons, fluorinated alkenes, fluorinated ethers, fluorinated polyethers, fluorinated amines, fluorinated hydrides and derivatives thereof.

42. The method of claim 36 wherein said fluorocarbon further comprises a bioactive agent.

43. A method for imaging an articular region comprising the steps of: administering an effective contrast enhancing amount of a neat fluorocarbon liquid to at least one synovial cavity; and imaging at least a portion of said synovial cavity.

44. The method of claim 43 wherein said bioactive agent is associated with a polymeric drug delivery vehicle.

45. The method of claim 42 wherein said bioactive agent comprises a radioactive compound.

46. The method of claim 36 wherein said fluorocarbon comprises a liquid fluorocarbon and said liquid fluorocarbon is administered by intra-articular injection.

47. The method of claim 36 further comprising the step of imaging at least a portion of the articular region following administration of said fluorocarbon.

48. The method of claim 47 wherein said imaging step comprises a imaging technique selected from the group consisting of magnetic resonance imaging, conventional radiography, computed tomography and ultrasound.

* * * * *